(12) United States Patent
Levinson

(10) Patent No.: US 6,195,575 B1
(45) Date of Patent: Feb. 27, 2001

(54) FETAL SENSOR WHICH SELF-INFLATES USING CAPILLARY FORCE

(75) Inventor: Mitchell Levinson, Pleasanton, CA (US)

(73) Assignee: Nellcor Puritan Bennett Incorporated, Pleasanton, CA (US)

(*) Notice: Subject to any disclaimer, the term of this patent is extended or adjusted under 35 U.S.C. 154(b) by 173 days.

(21) Appl. No.: 08/832,013

(22) Filed: Apr. 2, 1997

(51) Int. Cl.$^7$ .................................................. A61B 5/00

(52) U.S. Cl. ........................................ 600/338; 600/323

(58) Field of Search ........................... 600/310, 313, 600/315, 323, 338, 351, 376, 511, 591; 29/446, 825, 593, 595; 264/321

(56) References Cited

U.S. PATENT DOCUMENTS

| 3,306,966 | * | 2/1967 | Matejcek et al. | 264/321 |
| 3,903,232 | * | 9/1975 | Wood et al. | 264/321 |
| 4,768,522 | * | 9/1988 | Shapiro | 600/591 |
| 5,247,932 | * | 9/1993 | Chung et al. | 600/338 |

\* cited by examiner

*Primary Examiner*—Eric F. Winakur
(74) *Attorney, Agent, or Firm*—Townsend and Townsend and Crew LLP

(57) ABSTRACT

A fetal sensor with a biasing mechanism for biasing the sensor against the fetus, with the biasing mechanism being automatically self-inflating and insertable in compressed form. The biasing mechanism in a preferred embodiment is a compressed foam or sponge which expands upon being exposed to fluid, such as amniotic fluid within the uterus. Thus, the biasing mechanism can be compressed to allow easy insertion, and then can expand once in place to provide the pressure needed to hold the sensor against the fetus.

14 Claims, 2 Drawing Sheets

FETAL SENSOR WHICH SELF-INFLATES USING CAPILLARY FORCE

BACKGROUND OF THE INVENTION

The present invention relates to a non-invasive fetal intrauterine sensor, in particular a pulse oximeter sensor.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

Known non-invasive sensors include devices that are secured to a portion of the body, such as a finger, ear or the scalp. In animals and humans, the tissue of these body portions is perfused with blood and the tissue surface is readily accessible to the sensor.

It is desirable that photoelectric pulse oximetry also be useful for monitoring the blood flow characteristics and constituents of a fetus. For example, monitoring fetal oxygen levels provides an effective way to detect and provide indications for treating hypoxia in the fetus during labor. However, known sensors adapted for use on infants or adults are not suited for intrauterine placement.

The environment in which the non-invasive intrauterine sensor must operate is fluid-filled (e.g., by amniotic fluid) and is only accessible through the restricted opening of the cervix. Visual inspection of the fetus and the sensor is likewise restricted. Moreover, the operating environment presents certain variants that interfere with detection of the fetal blood flow characteristics using known pulse oximetry techniques. For example, the presence of the waxy vernix caseosa, hair, mucus, blood and dead tissue cells on top of the fetal tissue surface against which the sensor is to be positioned create a problem in establishing contact between the optical components of the sensor and the surface of blood-perfused tissue. Detection of fetal blood flow characteristics by pulse oximetry is particularly complicated by the relatively low perfusion and low oxygen saturation of blood in fetal tissue. These environmental factors prevent known sensors from providing reliable information needed to calculate fetal blood characteristics.

It is known that positive attachment of a sensor to the tissue surface improves the quality of the photoelectric signal provided by the sensor. Positive attachment to a human's tissue may be obtained by vacuum, adhesives, tapes or devices such as clothespin-type clips. However, fetal tissue is relatively moist and there is limited access to the tissue surface. Consequently, conventional adhesives or tapes or clips are not adapted for intrauterine use.

U.S. Pat. No. 5,247,932 shows a bladder between the fetus and the uterine wall which presses the active face of the sensor against the fetus' skin. U.S. Pat. No. 5,377,675 discloses a sensor using a fulcrum to bias the sensor against the fetus.

SUMMARY OF THE INVENTION

The present invention provides a fetal sensor with a means for biasing the sensor against the fetus, with the biasing means being automatically self-inflating and insertable in compressed form. The biasing means in a preferred embodiment is a compressed foam or sponge which expands upon being exposed to fluid, such as amniotic fluid within the uterus. Thus, the biasing means can be compressed to allow easy insertion, and then can automatically expand once in place to provide the pressure needed to hold the sensor against the fetus.

Preferably, the biasing means is made of an open-cell foam or sponge, with the foam or sponge cells being connected by capillaries to provide a capillary force for maximum expansion upon exposure to fluid. The foam is preferably covered with a smooth material, such as silicone, for minimizing friction during insertion and facilitating cleaning of the sensor. The cover has an opening for allowing the fluid to enter the internal foam.

For a further understanding of the nature and advantages of the invention, reference should be made to the following description taken in conjunction with the accompanying drawings.

DESCRIPTION OF THE PREFERRED EMBODIMENT

Figure 1:
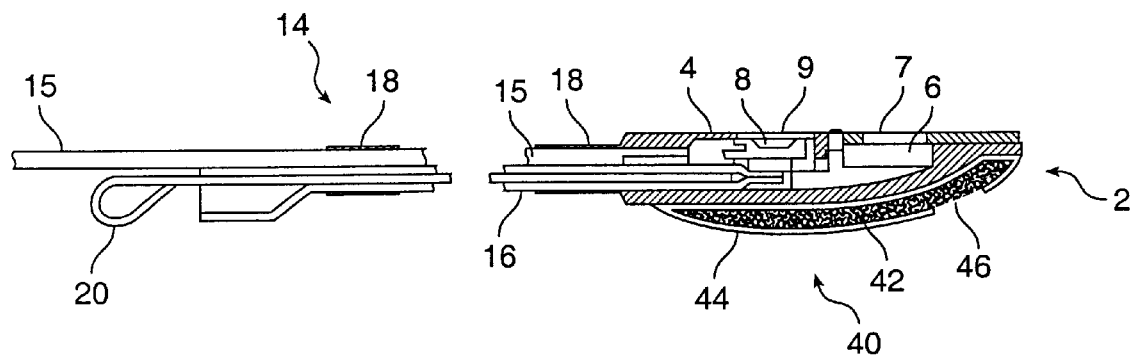
FIG. 1 is a side, cross-sectional view of a sensor with a compressed biasing means according to one embodiment of the present invention.

FIG. 1 shows a side cross-sectional view of a sensor apparatus according to a preferred embodiment of this invention. The sensor could be a pulse oximeter, ECG, IUP or other sensor. An embodiment with a pulse oximeter sensor will be described. Pulse oximetry sensor 2 comprises a resilient housing 4 which is formed from an elastomer such as silicone rubber or Santoprene so that the sensor is able to bend a small amount longitudinally to conform to the shape of the site.

One embodiment of a sensor to which the biasing means can be attached is set forth in U.S. patent application Ser. No. 08/556,619, filed Nov. 13, 1995, the disclosure of which is incorporated herein by reference. A brief description of one embodiment follows. An electromagnetic radiation directing unit 6 and an electromagnetic radiation detecting unit 8 are disposed in housing 4 to form the active face of the sensor. Radiation directing unit 6 preferably comprises a first red light emitting diode (LED) and a second infrared LED (not shown). Electromagnetic detecting unit 8 is a standard photodetector which may be shielded by a Faraday shield to prevent electromagnetic interference. An encoder 41 such as a resistor, provides a signal indicative of the wavelength of radiation directing unit 6. A description of such an encoding resistor is found in U.S. Pat. No. 4,621, 643, the disclosure of which is incorporated herein by reference. Radiation directing unit 6 and radiation detecting unit 8 are coupled to wires (not shown) which form a bus communicating with oxygen saturation calculating unit in a remote oximeter monitor (not shown). Any exposed parts of the wires may also be shielded by a grounded Faraday shield. Clear lenses 7 and 9 cover units 6 and 8, respectively.

In addition, the optical components and the electrode on the active face of the sensor may be disposed on a standard fiberglass circuit board with conductive traces forming (in part) the buses communicating with the electrodes and optical components. Alternately, a flexible substrate, such as polyester, may be used to support the electronics. The sensor body may be molded around the circuit board or flexible substrate, with appropriate openings formed in the body for the electrodes and optical components.

Figure 3:
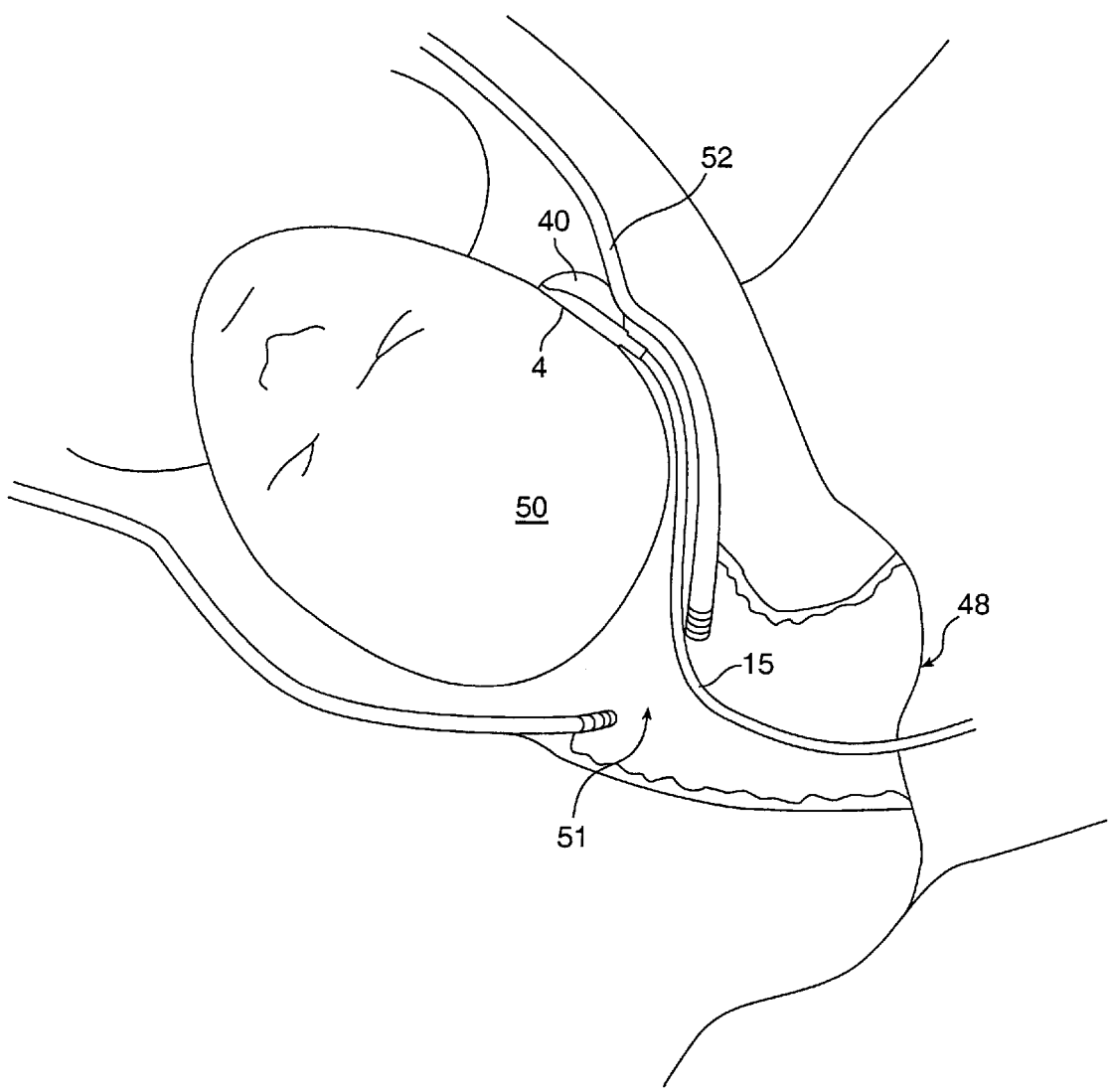
FIG. 3 is a view showing the sensor in place in the preferred region.

Affixed to housing 4 of the preferred embodiment shown in FIG. 3 is a handle 14 which functions as an insertion and placement aid. Handle 14 comprises a substantially flat guide tube 16 which, together with the cable 15 containing the wires coupled to units 6 and 8, is enclosed by a tube 18 which may comprise heat shrink tubing. A removable stiffener 20 is disposed within guide tube 16 before shrinking tube 18. Stiffener 20 ensures that handle 14 has the desired property of allowing bending along the fetal head and the curve of the mother's pelvis toward the region to be probed while resisting lateral bending.

A biasing means 40 partially covers housing 4 to provide a sensor retention feature. Biasing means 40 is made, e.g., of a resilient, open-celled polyurethane foam or sponge 42 surrounded by a silicone skin 44 in which a small opening 46 has been formed. The function of biasing means 40 is to press the active face of sensor housing 4 firmly against the fetus at the sensor site and to keep the sensor in place during the contractions associated with labor.

Figure 2:
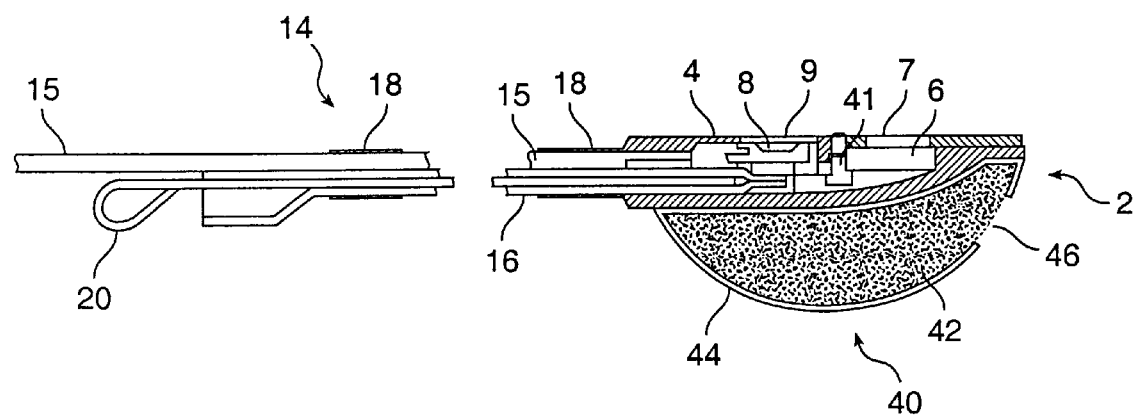
FIG. 2 is the view of FIG. 1 with an expanded biasing means.

As shown in FIG. 1, biasing means 40 is compressed to give the sensor a thinner profile for insertion into the uterus. Upon insertion into the uterus, amniotic fluid can enter through opening 46, and the biasing means will expand to the shape shown in FIG. 2 as the fluid is absorbed by the foam or sponge.

In an alternate embodiment, biasing means skin or cover 44 could be eliminated, leaving the foam or sponge exposed to the surroundings. Preferably, the foam or sponge has a series of open cells connected by capillaries into which fluid can flow to provide greater expansion force.

During the manufacture of a sensor as shown in FIG. 1, the biasing means 40 can be immersed in a fluid and then allowed to dry while under compression. Upon drying, it will retain its compressed shape, and can be attached to the back of the sensor housing 4. Upon insertion into the uterus, fluid will enter through opening 46, penetrating the cells of the biasing means and causing it to expand into the shape shown in FIG. 2. This will press the sensor face against the fetus 50, as illustrated in FIG. 3.

Preferably, cover or skin 44 is a compliant, stretchable material which allows sufficient expansion of the foam or sponge inside of it, and also will smoothly cover the foam or sponge in its compressed state.

As shown in FIG. 3, the sensor is inserted into a vagina 48 past cervix 51 and up alongside the scalp of a fetus 50. At this position, biasing means 40, when expanded, presses up against the uterine wall 52, forcing the sensor housing 4 against the fetus.

As will be understood by those of skill in the art, the present invention may be embodied in other specific forms without departing from the spirit or essential characteristics thereof. For example, the biasing means could be attached to a different position of the housing, multiple biasing means could be used, or the opening could be placed in a different position, or multiple openings in the biasing means could be used. Accordingly, the above embodiments are intended to be illustrative, but not limiting, of the scope of the invention which is set forth in the following claims.

What is claimed is:

1. A sensor comprising:
   a housing having front and back sides;
   a sensor element mounted in said front side of said housing; and
   a biasing means attached to said back side of said housing for biasing said sensor element against a patient site, said biasing means having an initial relaxed position which is compressed, said biasing means being expandable upon the absorption of fluid.

2. The sensor of claim 1 wherein said sensor element comprises:
   a radiation emitter mounted in said front side of said housing; and
   a radiation detector mounted in said front side of said housing.

3. The sensor of claim 2 wherein said sensor is a pulse oximeter sensor.

4. The sensor of claim 2 further comprising an encoder configured to provide a signal indicative of the wavelength of said radiation emitter.

5. The sensor of claim 1 wherein said biasing means comprises an open cell foam.

6. The sensor of claim 4 further comprising a resilient, solid cover over said biasing means, said cover including an opening for allowing fluid to enter said biasing means.

7. The sensor of claim 6 wherein said cover is silicone.

8. The sensor of claim 4 further comprising a plurality of capillaries interconnecting open cells of said foam.

9. The sensor of claim 1 wherein said biasing means comprises a sponge.

10. A pulse oximeter sensor comprising:
    a housing having front and back sides;
    a radiation emitter mounted in said front side of said housing;
    a radiation detector mounted in said front side of said housing; and
    a biasing means attached to said back side of said housing for biasing said radiation emitter and said radiation detector against a patient site, said biasing means having an initial relaxed position which is compressed, said biasing means being expandable upon the absorption of fluid, said biasing means including
       an open cell foam,
       a resilient, solid cover over said open cell foam, and
       an opening in said cover for allowing fluid to enter said biasing means.

11. The sensor of claim 10 wherein said cover is silicone.

12. The sensor of claim 10 further comprising a plurality of capillaries interconnecting open cells of said foam.

13. A method for manufacturing a sensor comprising the steps of:
    providing a housing having front and back sides;

mounting a sensor element in said front side of said housing;

providing a biasing means for biasing said sensor element against a patient site, said biasing means having an initial relaxed position which is compressed; and attaching said biasing means to said back side of said housing, said biasing means being expandable upon the absorption of fluid.

14. The method of claim 13 wherein said step of providing said biasing means comprises the steps of:

applying a fluid to said biasing means;

compressing said biasing means; and allowing said biasing means to dry while under compression.

* * * * *